United States Patent [19]
Habraken et al.

[11] Patent Number: 5,325,413
[45] Date of Patent: Jun. 28, 1994

[54] X-RAY EXAMINATION APPARATUS

[75] Inventors: Wilhelmus J. P. Habraken; Johannes G. Van Endschot, both of Eindhoven, Netherlands

[73] Assignee: U.S. Philips Corporation, New York, N.Y.

[21] Appl. No.: 968,608

[22] Filed: Oct. 29, 1992

[30] Foreign Application Priority Data

Oct. 30, 1991 [EP] European Pat. Off. ........ 91202802.4

[51] Int. Cl.$^5$ .......................................... G03B 42/02
[52] U.S. Cl. ..................... 378/181; 378/197
[58] Field of Search ............... 378/167, 181, 195, 196, 378/197

[56] References Cited

U.S. PATENT DOCUMENTS

| | | | |
|---|---|---|---|
| 4,358,856 | 11/1982 | Stivender et al. | 378/167 |
| 4,363,128 | 12/1982 | Grady et al. | 378/181 |
| 4,365,343 | 12/1982 | Grady et al. | 378/181 |
| 4,761,805 | 8/1988 | Sebring | 378/181 |
| 4,879,736 | 11/1989 | Bergman et al. | 378/181 |
| 5,111,496 | 5/1992 | Van Es et al. | 378/181 |

Primary Examiner—Craig E. Church
Attorney, Agent, or Firm—Jack D. Slobod

[57] ABSTRACT

In an x-ray examination apparatus, a film holder is mounted on a frame, which itself is connected to the carrier, notably a C-arm, for the x-ray source and the image intensifier. When not in use, the film holder can be placed in a park position against the inner circumference of the C-arm, such that the film holder neither obscures, nor impedes access to the patient (region). The frame with the film holder can be rotated to a standby position next to the image intensifier, such that the film holder can be conveniently reached for preparation for exposure. Finally, the film holder can be rotated with respect to the frame into an exposure position in front of the image intensifier. The C-arm remains balanced for all three positions of the film holder; this is achieved by two counterweights that move along the outer circumference of the C-arm, just under its outer enclosure. Consequently, the C-arm can be moved manually without considerable effort. Because in its park position the film holder does not protrude beyond the outer circumference of the C-arm, the motion of the C-arm is not restricted by the film holder.

8 Claims, 5 Drawing Sheets

X-RAY EXAMINATION APPARATUS

BACKGROUND OF THE INVENTION

1. Field of the Invention

The invention pertains to an x-ray examination apparatus that includes a carrier supporting an x-ray source for generating an x-ray beam, an x-ray detector facing the x-ray source, and a film holder, the film holder being displaceable between an exposure position in front of the x-ray detector and a standby position outside the x-ray beam path.

2. Description of the Related Art

An x-ray examination apparatus having the possibility of optionally employing either an x-ray detector, notably an x-ray image intensifier, or a film holder has been described in U.S. Pat. No. 4,879,736.

In U.S. Pat. No. 4,879,736 the film holder is pivotable from a standby position to an exposure position, the film holder remaining attached to the image intensifier. The film holder is mounted on a bearing surrounding the image intensifier, so that it can be displaced between various standby positions around the image intensifier. The apparatus described in the cited Patent Specification is not balanced. Consequently, a powerful system of motors and brakes is needed for displacing the film holder between its standby and exposure positions and for moving the carrier; therefore the carrier having the form of a C-shaped support cannot be moved manually without considerable effort.

It is inter alia an object of the invention to provide an x-ray examination apparatus in which alternatively an x-ray detector or a film holder can be used, such that the film holder neither obscures, nor impedes access to the patient when not in use.

To achieve this, an x-ray examination apparatus in accordance with the invention is characterised in that the film holder is mounted movably on a frame which itself is movably connected to the carrier, the film holder with the frame being displaceable between a park position against an inner circumference of the carrier and a standby position next to the x-ray detector, and the film holder being displaceable between the standby position and an exposure position located in front of the x-ray detector.

The film holder can by choice be positioned either in a park position where the frame is positioned against an inner circumference of the carrier, or in a standby position, in which the film holder is positioned next to the x-ray detector, notably an x-ray image intensifier, and an input screen of the image intensifier and an image recording plane in the film holder are preferably situated substantially in a common plane perpendicular to the central ray, or the film holder an be positioned in an exposure position in which it is orthogonal to a central ray and the image recording plane in the film holder is situated at a distance to the x-ray source which is equal to the distance between the x-ray detector to the x-ray source when the film holder is in its standby position.

Because in its park position the film holder and the frame supporting it are positioned against the inner circumference of the carrier and near a suspension of the carrier from its vertical support, it is achieved that the patient region is vacated by the film holder and that, moreover, vision and access to the patient (region) are not impeded by the film holder when it is not being used. Furthermore, the film holder in its park position does not protrude beyond an outer circumference of the carrier, so that even in its park position the film holder does not restrict the motion of the carrier.

The frame supporting the film holder is mounted pivotably about an axis perpendicular to the plane of the carrier. The film holder can be moved to its standby position by rotation of the frame around this axis. In this standby position the film holder is next to the image intensifier and in the same plane as the input screen of the image intensifier. In this standby position, the film holder is approximately level with the connection of the carrier to its vertical stand. In this position the film holder is situated next to the patient region and preferably so high above the floor that it is conveniently reached by a person standing next to the x-ray examination apparatus. Consequently, in the standby position the film holder can be conveniently prepared for exposure, i.e. installing or removing film cassettes, positioning the patient or collimating the x-ray beam, without disturbance to the patient or life support systems.

The film holder is mounted pivotably on the frame such that it can be rotated about an axis orthogonal to the frame so as to reach the exposure position. In the exposure position the film holder and the x-ray detector have a common image axis, so that x-radiation transmitted through the film holder can be employed, using the x-ray detector, to monitor the image formed on the film.

It is to be noted that the balancing of the motion of the film holder by means of a counterweight which moves in the opposite direction is known per se from U.S. Pat. No. 4,358,856.

SUMMARY OF THE INVENTION

It is an object of this preferred embodiment to enable movement without considerable effort of the film holder between its three alternative positions as well as easy movement of the C-shaped support when the film holder is in either of its three alternative positions. In a preferred embodiment of the invention the carrier in the form of a C-shaped support, also referred to hereinafter as 'C-arm' remains balanced in all three positions of the film holder. To achieve this, there are provided two counterweights that are movable within the outer circumference of the C-arm.

One counterweight is moved in order to restore the balance when the frame with the film holder is displaced between its park position and its standby position. The other counterweight is moved in order to restore the balance when the film holder is displaced between its standby position and its exposure position. Because the film holder is not attached to the image intensifier the mass of the counterweights may be small. As a consequence the counterweights employed can be constucted to be so flat that they can move within the outer circumference of the C-arm, just under its outer enclosure. Hence there is no need for a voluminous stand accommodating large counterweights as described in the cited Patent Specification, so that access to the patient zone is further improved. Should it happen that the image intensifier collides with the patient, the mass of the film holder and its counterweight will not be involved in the collision, so that the impact of such a collision is substantially less than in an apparatus where the film holder remains attached to the image intensifier. Moreover, as light counterweights are employed, no powerful system of motors and brakes need be used, so that the C-arm can be moved manually without considerable effort.

In a further preferred embodiment the motions of the film holder and its counterweights during displacement of the film holder between its park position and its standby position and between its standby position and its exposure position, respectively are controlled by two low-power motors, each motor driving the coupled system of the film holder and a respective counterweight, specifically the coupling being provided by a combination of gear-wheels, sheaves and belts or chains.

In a further embodiment the film holder comprises a film exchanger for film transport when a plurality of exposures are to be made.

An embodiment of an x-ray examination apparatus will be described in detail hereinafter with reference to the accompanying drawings wherein:

FIGS. 1a–c show a side elevation of an x-ray examination apparatus in accordance with the invention. FIG. 1a shows the film holder in its park position; in FIG. 1b the film holder is in its standby position and lastly, FIG. 1c shows the film holder in its exposure position.

FIGS. 2a, b show the mechanism for the coupling of the motions of the film holder and the counterweights.

FIG. 3 is a plan view of the film holder and the frame whereto it is connected.

DETAILED DESCRIPTION OF THE PREFERRED EMBODIMENTS

Figure 1A:
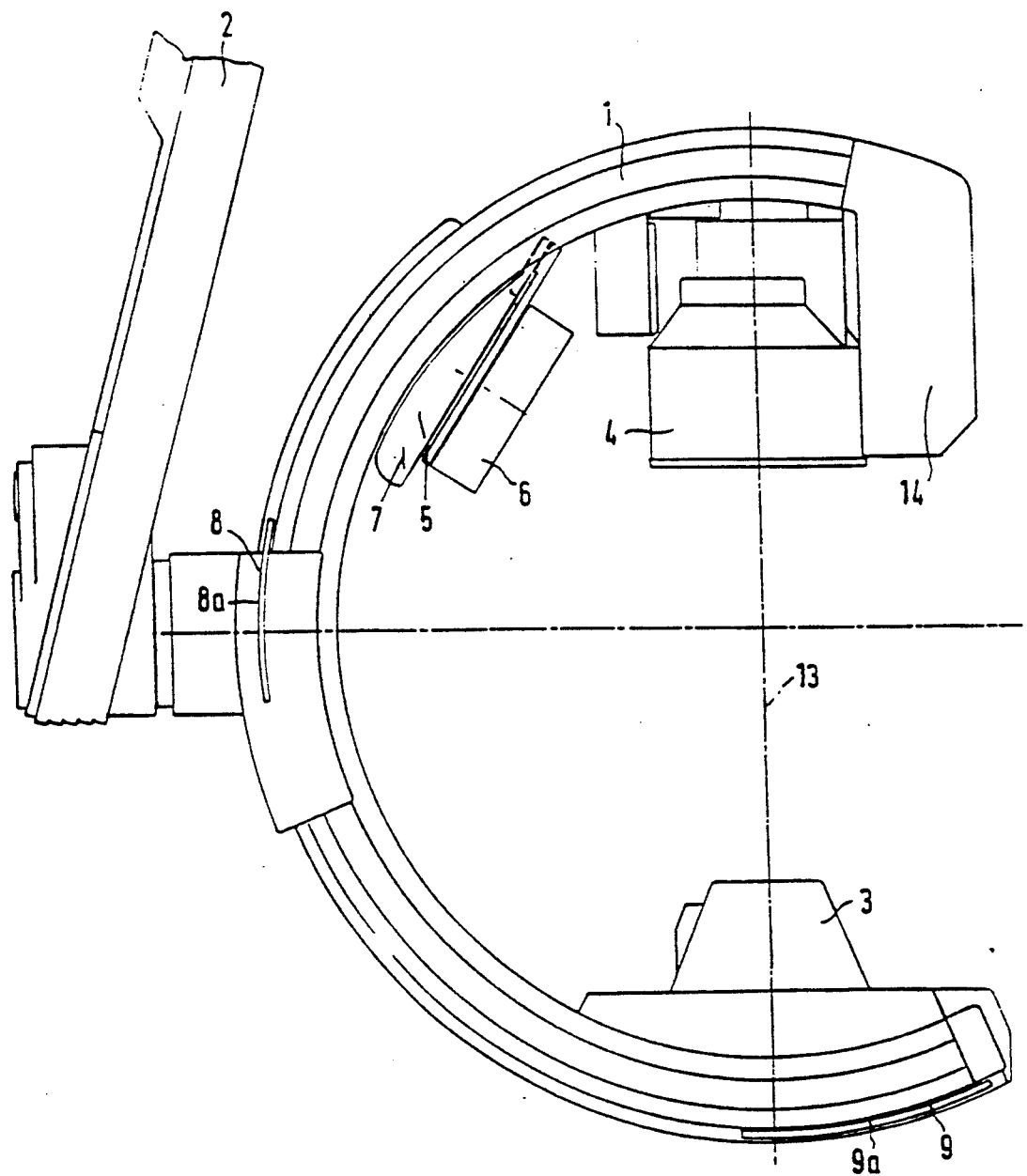
Figure 1:
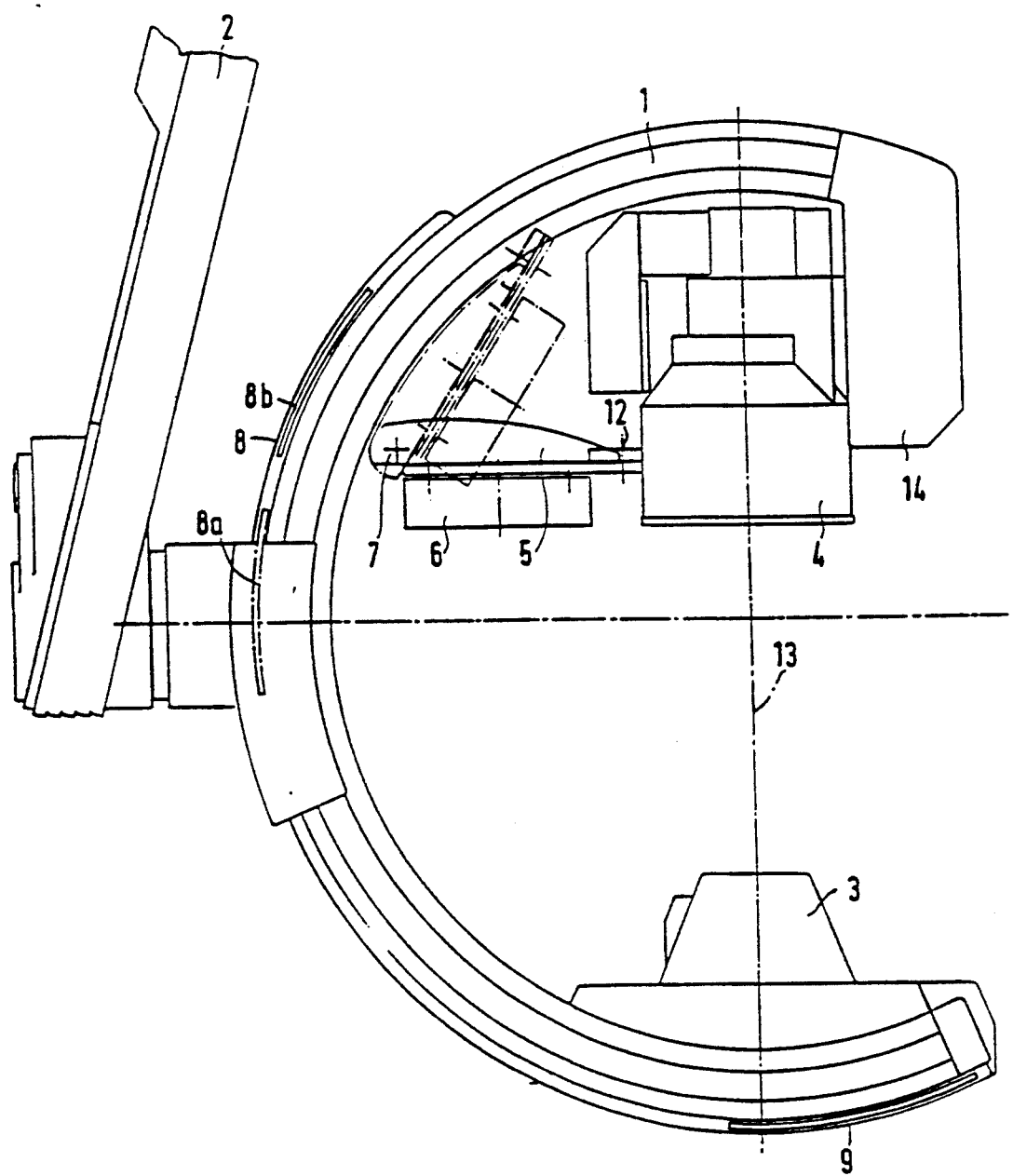
Figure 1:
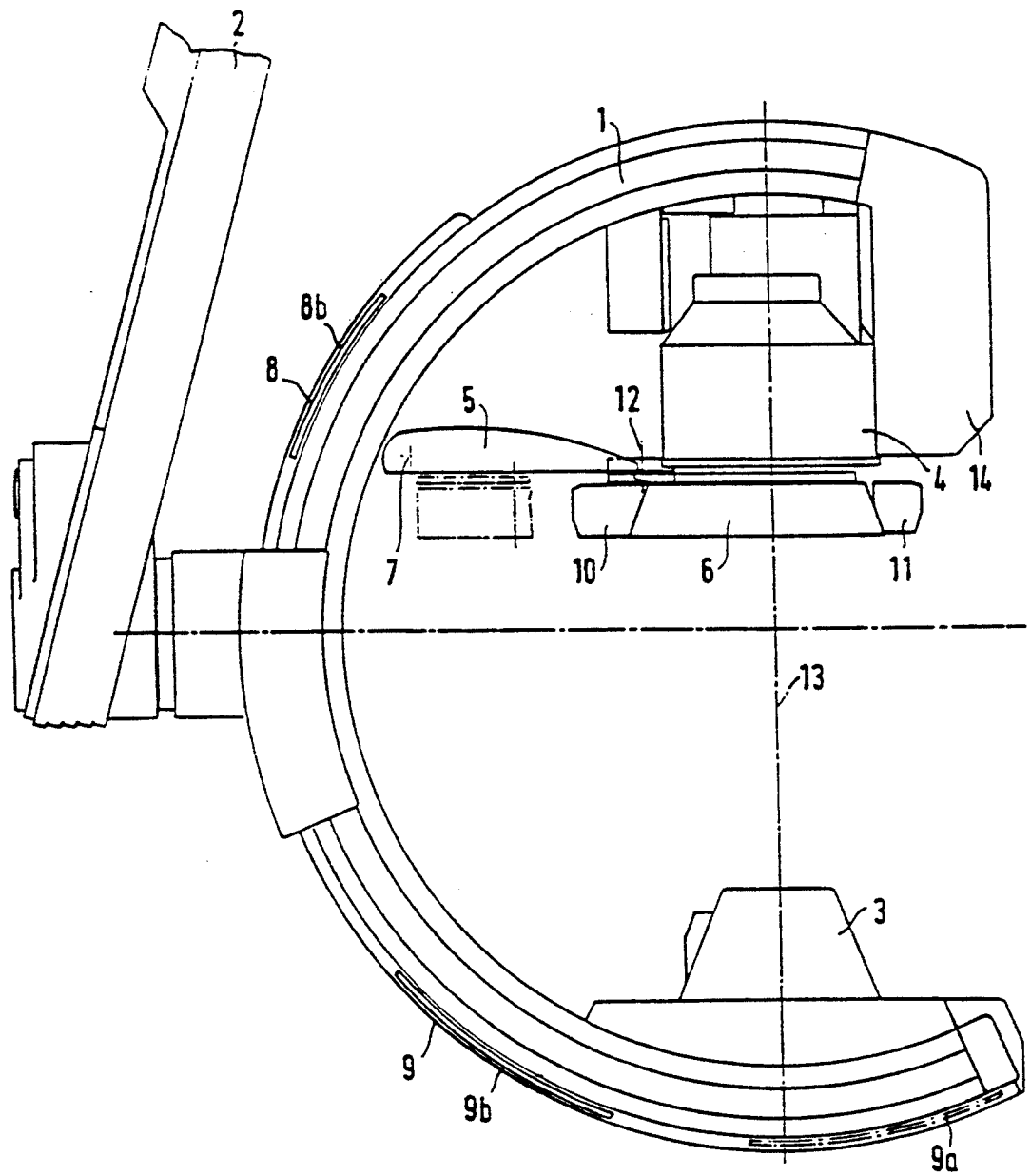

FIGS. 1a–c show a C-shaped carrier 1 mounted on a predominantly vertical support 2 and supporting an x-ray source 3, and an x-ray detector 4, and a frame 5. In the embodiment depicted here the x-ray detector is an x-ray image intensifier. A film holder 6 is mounted on the frame 5. Two counterweights 8 and 9 are provided. Each of the FIGS. 1a–c shows the positions of the counterweights for the respective positions of the film holder. In FIG. 1a the film holder is shown in its park position. In order to move the film holder 6 into its standby position, the frame can rotate about an axis 7. In their positions 8a and 9a, as shown in FIG. 1a, the counterweights 8 and 9, respectively, balance the film holder and the frame, thus balancing the entire C-arm, i.e. the C-shaped carrier and the film holder, the image intensifier and the x-ray source. When the film holder is moved to its standby position, as shown in FIG. 1b, by rotation of the frame through about 45°, the counterweight 8 is moved to a position 8b as shown in FIG. 1b, so that the balance is sustained. In FIG. 1c, the film holder is shown with two film cassettes 10 and 11 attached to it. The film holder can be moved to its exposure position by rotating the film holder approximately 90° about an axis 12. Simultaneously, the counterweight 9 is moved to a position 9b as indicated in FIG. 1c, so that the balance of the entire C-arm is maintained when the film holder is moved to its exposure position. For the movement of the film holder to its exposure position, the image intensifier is moved away from the x-ray source along an axis 13, so that the film holder can be positioned in approximately the same plane as occupied by the input screen of the image intensifier when the film holder is in its standby position. The motion of the image intensifier along the axis 13 is counterbalanced by counterweights accommodated in a housing 14; this known counterbalancing mechanism will not be described in detail here.

Figure 2:
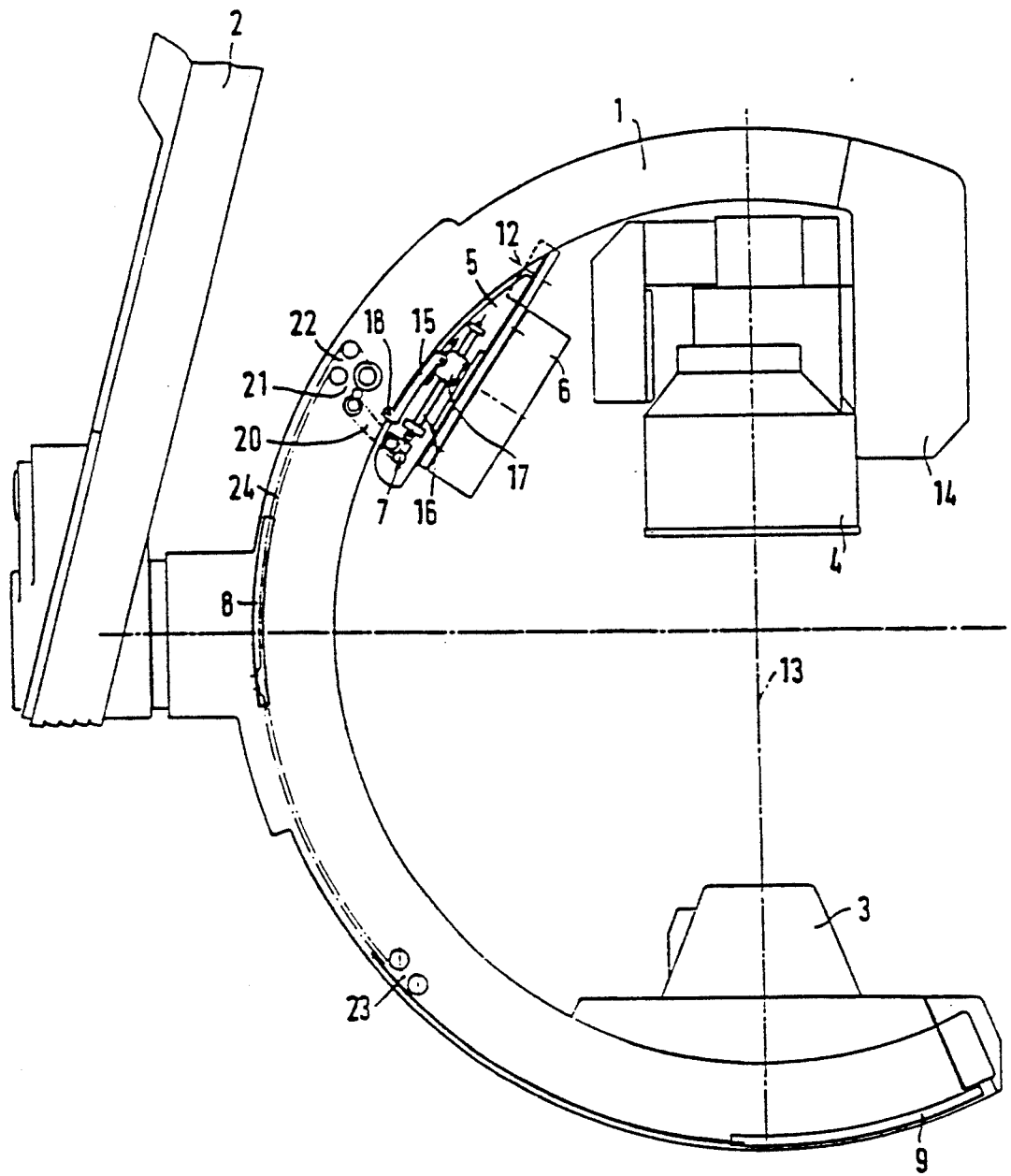
Figure 2B:
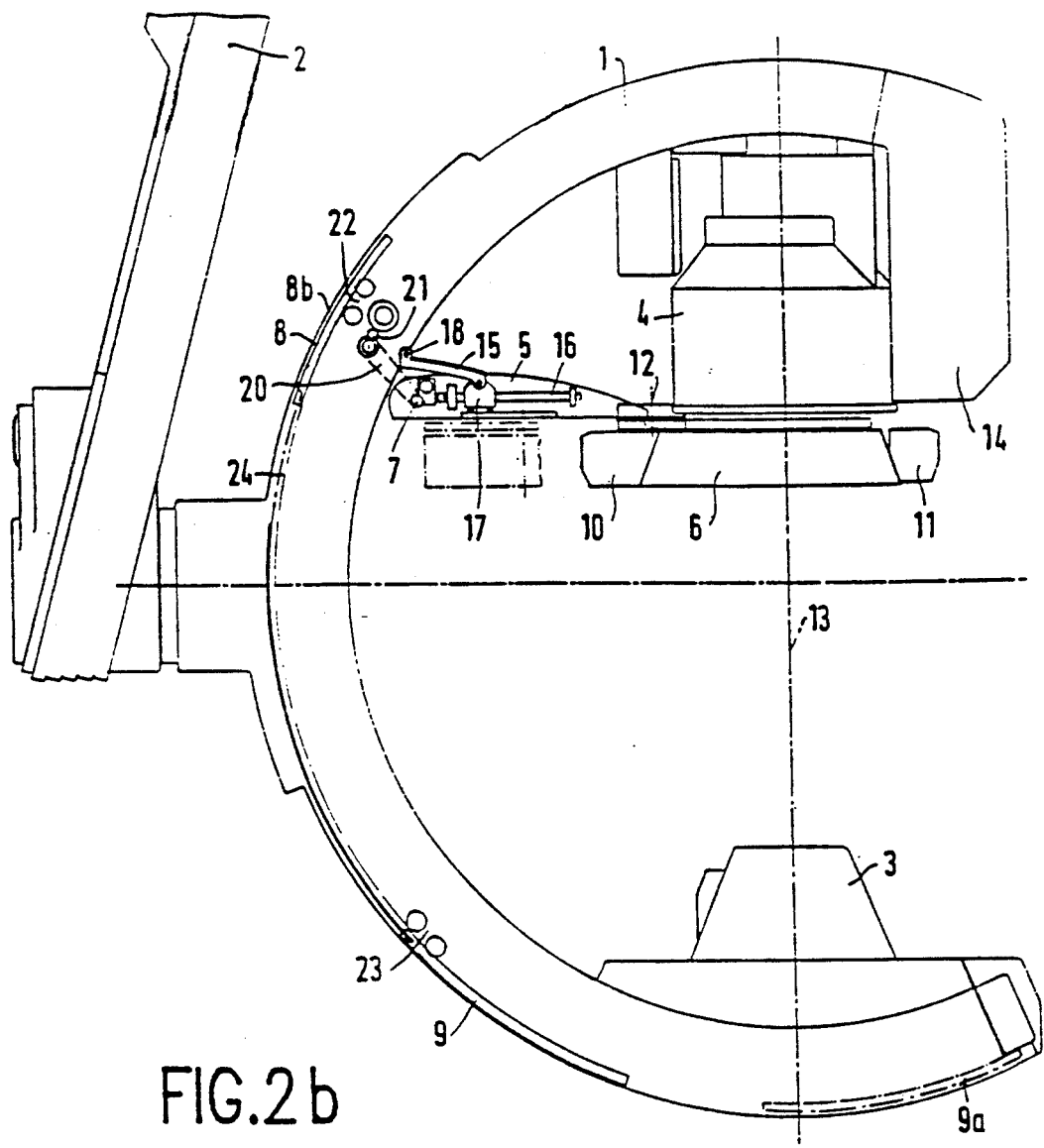

FIG. 2a shows the same side elevation as FIGS. 1a–c, but with details of the coupling and drive mechanisms for the motions of the film holder and the associated counterweights. The frame 5 is mounted rotatably around the axis 7. The frame is held in position by means of an arm 15, a spindle 16 and a member 17. The spindle 16 is mounted on the frame 5. The member 17 is moved in the directions of the arrows in dependence on whether the spindle is rotated clockwise or anticlockwise around its longitudinal axis by a motor 19 (in FIG. 3). The arm 15 is thus rotated about 45° around an axis 18, so that the film holder is moved from its park position shown in FIGS. 1a and 2a to its standby position as shown in FIGS. 1b and 2b. Via the spindle 16, the motor 19 (in FIG. 3) also drives a system 20 of sheaves and belts that itself drives a gear-wheel assembly 21, a system of sheaves 22 and 23 and a belt 24 that runs along the outer circumference of the C-arm to displace the counterweight 8 between its positions for balancing the apparatus, when the film holder is in its park position or in its standby position, respectively.

The motion of the film holder between its standby position and its exposure position and the corresponding motion of the counterweight 9, will first be described with reference to FIG. 3. A second motor, denoted by the reference 25, rotates a second spindle, denoted by the reference 26, and mounted on the frame 5, about its longitudinal axis, so that a body 27 is moved in the directions of the arrows, in dependence on the direction of rotation of the spindle 26. As a consequence of the motion of the member 27, an arm 28 is moved between its position 28a drawn in solid lines and its position 28b drawn in dashed-dotted lines. As a result a disk 29 is rotated about 90° around the axis 12, so that the film holder 6, being rigidly attached to the disk 29, is moved between its standby position 6a, drawn in dashed-dotted lines and its exposure position 6b, drawn in solid lines.

The description will now be continued with reference to FIG. 2b. The side elevation presented therein illustrates the position of the frame 5, the arm 15 and the body 17 with respect to the spindle 16 for the situation where the film holder is in its standby position, indicated by the phantom contours, and in its exposure position, drawn in solid lines.

The motion of the counterweight 9 for maintaining the balance of the apparatus when the film holder is moved between its standby position and its exposure position is controlled by the motor 25 that drives, via a spindle 26, a system of sheaves and belts, which is similar to the system 20, positioned behind the system 20 as determined by the line of view in FIGS. 2a,b, but not visible in FIGS. 2a,b because the view is obscured by the system 20. The system of sheaves and belts driven by motor 25 drives a second gear-wheel assembly, similar to the assembly 21, but which is not visible in FIGS. 2a,b, because the view is now obscured by the gear-wheel assembly 21. The second gear-wheel assembly and a system of sheaves and a belt resembling the system constituted by the sheaves 22 and 23 and the belt 24, displaces the counterweight 9 between its positions 9a and 9b, in which it balances the apparatus when the film holder is in its standby position and in its exposure position, respectively.

Figure 3:
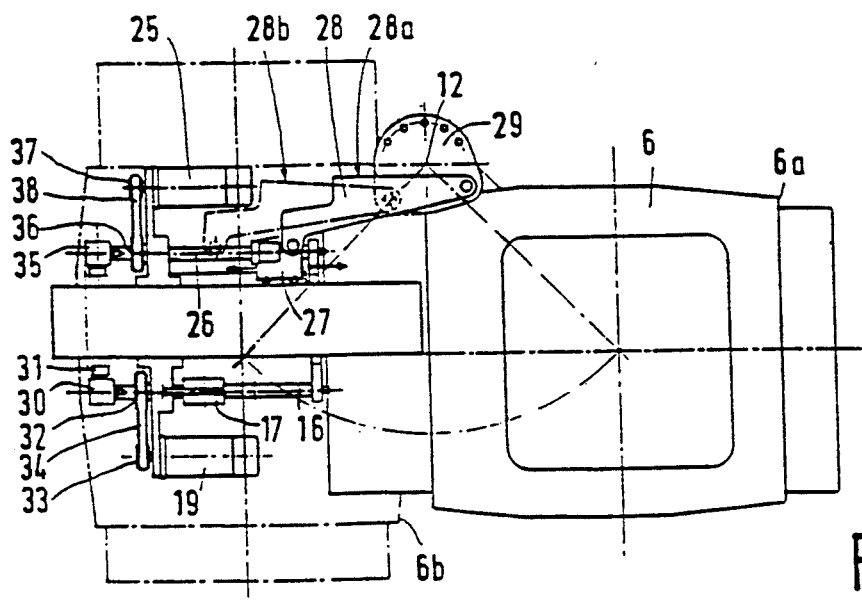

The description will now be continued with reference to FIG. 3. A pinion 30 couples of the motion of the spindle 16 to the sheave 31, that is part of the system 20. Hence, via the system of sheaves 32, 33 and a belt 34, the motor 19 drives the frame with film holder so as to move between its park position and its standby position, and at the same time drives the counterweight 8 so as to move between the positions 8a and 8b, corresponding to the park position of the film holder as shown in FIG. 1a and to the standby position of the film holder as shown in FIG. 1b, respectively. Similarly, a further pinion 35 in conjunction with a system of sheaves 36, 37 and a belt 38 the motor 25 drives the film holder 6 so as to move between its standby position and its exposure position, and at the same time drives the counterweight 9 so as to move between the positions 9a and 9b, corresponding to the standby position of the film holder as shown in FIG. 1b and to the exposure position of the film holder as shown in FIG. 1c, respectively.

We claim:

1. An x-ray examination apparatus that comprises a carrier supporting an x-ray source for generating an x-ray beam, an x-ray detector facing the x-ray source, and a film holder, the carrier being suspended from a column, the film holder being displaceable between an exposure position in front of the x-ray detector and a standby position outside the x-ray beam path, characterised in that the film holder is mounted movably on a frame which itself is movably connected to the carrier, the film holder with the frame being displaceable between a park position against an inner circumference of the carrier and a standby position next to the x-ray detector, the film holder being displaceable between the standby position and an exposure position located in front of the x-ray detector.

2. An x-ray examination apparatus as claimed in claim 1, characterised in that in the standby position the film holder is positioned next to the x-ray detector and the image recording plane in the film holder is situated in a plane which is substantially the same as that of the input screen of the x-ray detector.

3. An x-ray examination apparatus as claimed in claim 1, characterised in that the carrier has the form of a C-shaped support and in that there are provided two counterweights that are moveable within an outermost circumference of the C-shaped support; a first counterweight being movable so as to compensate substantially a shift of a centre of gravity of the film holder and the frame that occurs upon displacement the film holder with the frame between the park position and the standby position and a second counterweight being moveable so as to compensate substantially a shift of a centre of gravity of the film holder that occurs when the film holder is displaced between its standby position and its exposure position.

4. An x-ray examination apparatus as claimed in claim 3, characterised in that said counterweights are constructed to be so flat, that can move along the outer circumference of the C-shaped support.

5. An x-ray examination apparatus as claimed in claim 3, characterised in that each combination formed by a counterweight, and the frame and the film holder is linked to respective elements that ensure concerted movements of the frame, the film holder and the relevant counterweight.

6. An x-ray examination apparatus as claimed in claim 5, characterised in that there are provided two motors, each of which driving one of said combinations.

7. An x-ray examination apparatus as claimed in claim 5, characterised in that there are provided one motor and two clutches via which each of said combinations is driven at option.

8. An x-ray examination apparatus as claimed in claim 1, characterised in that the film holder comprises a film exchanger.

* * * * *